US011279960B2

(12) United States Patent
Kasahara et al.

(10) Patent No.: US 11,279,960 B2
(45) Date of Patent: Mar. 22, 2022

(54) METHOD OF PRODUCING XYLO-OLIGOSACCHARIDE

(71) Applicant: Toray Industries, Inc., Tokyo (JP)

(72) Inventors: Takuya Kasahara, Kamakura (JP); Chiaki Yamada, Kamakura (JP); Hiroyuki Kurihara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 210 days.

(21) Appl. No.: 16/089,057

(22) PCT Filed: Mar. 30, 2017

(86) PCT No.: PCT/JP2017/013380
§ 371 (c)(1),
(2) Date: Sep. 27, 2018

(87) PCT Pub. No.: WO2017/170919
PCT Pub. Date: Oct. 5, 2017

(65) Prior Publication Data
US 2020/0216869 A1 Jul. 9, 2020

(30) Foreign Application Priority Data

Mar. 31, 2016 (JP) .............................. JP2016-070758

(51) Int. Cl.
*C12P 19/04* (2006.01)
*C12P 19/14* (2006.01)
*C12N 9/42* (2006.01)
*C12N 9/24* (2006.01)

(52) U.S. Cl.
CPC ............ *C12P 19/04* (2013.01); *C12N 9/2437* (2013.01); *C12N 9/2445* (2013.01); *C12N 9/2482* (2013.01); *C12N 9/2485* (2013.01); *C12P 19/14* (2013.01); *C12Y 302/01008* (2013.01); *C12Y 302/01021* (2013.01); *C12Y 302/01037* (2013.01); *C12Y 302/01091* (2013.01)

(58) Field of Classification Search
CPC .. C12N 9/2437; C12N 9/2445; C12N 9/2482; C12N 9/2485; C12Y 302/01091; C12Y 302/01021; C12Y 302/01008; C12Y 302/01037
See application file for complete search history.

(56) References Cited

U.S. PATENT DOCUMENTS

2013/0203117 A1* 8/2013 Kurihara ................. C13K 1/02
435/72
2016/0040203 A1 2/2016 St. John et al.

FOREIGN PATENT DOCUMENTS

| CN | 101250567 A | 8/2008 |
| EP | 2548966 A1 | 1/2013 |
| EP | 3020820 A1 | 5/2016 |
| EP | 3438262 A1 | 2/2019 |
| JP | 2006-296224 A | 11/2006 |
| WO | 2010/067785 A1 | 6/2010 |
| WO | 2011/115040 A1 | 9/2011 |
| WO | 2015/005307 A1 | 1/2015 |

OTHER PUBLICATIONS

Poutanen et al. "Characteristics of Trichoderma reesei β-xylosidase and its use in the hydrolysis of solubilized xylans" Appl Microbiol Biotechnol (1988) 28:425-432 (Year: 1988).*
Kristufek et al. "Regulation of β-xylosidase formation by xylose in Trichoderma reesei" Appl Microbiol Biotechnol (1995) 42:713-717 (Year: 1995).*
Li et al. "Effect of pH on cellulase production and morphology of Trichodermareesei and the application in cellulosic material hydrolysis" Journal of Biotechnology 168 (2013) 470-477 (Year: 2013).*
BRENDA "Information on EC 3.2.1.37" 2 pgs updated Jan. 2021 (Year: 2021).*
The Extended European Search Report dated Oct. 25, 2019, of counterpart European Application No. 17775453.8.
Kyung Young Yoon et al., "Enzymatic production of pentoses from the hemicellulose fraction of corn residues," LWT—Food Science and Technology, vol. 39, Issue 4,May 2006, pp. 388-392 (Abstract).
Raj Kumar et al., "Biocnversion of lignocellulosic biomass: biochemical and molecular perspectives," Journal of Industrial Microbiology & Biotechnology, vol. 35, Issue 5, May 2008, pp. 377-391 (Abstract).
Ozlem Akpinar et al., "Production of xylooligosacchrides by controlled acid hydrolysis of lignocellulosic materials," Carbohydrate Research, vol. 344, Issue 5, Mar. 31, 2009, pp. 660-666 (Abstract).
Ayyappan Appukuttan Aachary et al., "Xylooligosaccharides (XOS) as an Emerging Prebiotic: Microbial Synthesis, Utilization, Structural Characterization, Bioactive Properties, and Applications," Comprehensive Reviews in Food Science and Food Safety, vol. 10, 2011.

(Continued)

*Primary Examiner* — Thane Underdahl
(74) *Attorney, Agent, or Firm* — DLA Piper LLP (US)

(57) ABSTRACT

A method produces xylo-oligosaccharides from a biomass containing xylan and cellulose, which method is convenient and has a high yield of xylo-oligosaccharides because of inhibition of degradation of xylo-oligosaccharides into xylose. In the method of producing xylo-oligosaccharides, a biomass containing xylan and cellulose is hydrolyzed with a cellulase composition having at least activities of xylanase, cellobiohydrolase and β-glucosidase and substantially free of β-xylosidase activity during hydrolysis.

10 Claims, No Drawings

(56) References Cited

OTHER PUBLICATIONS

Ana Flávia Azevedo Carvalho et al., "Xylo-oligosaccharides from lignocellulosic materials: Chemical structure, health benefits and production by chemical and enzymatic hydrolysis," Food Research International, vol. 51, Issue 1, Apr. 2013, pp. 75-85 (Abstract).

Patricia Moniz et al., "Hydrothermal production and gel filtration purification of xylo-oligosaccharides from rice straw," Industrial Crops and Products, vol. 62, Dec. 2014, pp. 460-465 (Abstract).

* cited by examiner

METHOD OF PRODUCING XYLO-OLIGOSACCHARIDE

TECHNICAL FIELD

This disclosure relates to a method of producing xylo-oligosaccharides from biomass containing xylan and cellulose.

BACKGROUND

Xylo-oligosaccharide is a general term of oligosaccharides formed by β-glycosidic linkages of a plurality of xylose units. Xylo-oligosaccharides are also used as a material for functional foods because of, for example, its excellent intestine-regulating function (Ayyappan A A et al., Compre. Rev. Food. Sci. Food Saf. 10, 2-16 (2011)).

Xylo-oligosaccharides can be obtained through hydrolysis of xylan contained in a biomass containing xylan and cellulose. Known hydrolysis methods include hydrothermal treatment method (Patricia M et al., Ind. Crops. Prod. 62, 460-465 (2014)), acid hydrolysis method (Ozlem A et al., Carbohydr. Res. 344, 660-666 (2009)), and enzyme treatment method using xylanase (JP 2006-296224 A).

Among these, hydrolysis of xylan with xylanase allows selective production of xylo-oligosaccharides, which enables efficient production of xylo-oligosaccharides. However, xylan, a substrate of xylanase, is a main component in hemicellulose, and hemicellulose in plant cells forms higher order structure with cellulose and lignin. Thus, to efficiently degrade xylan by xylanase, other processes of hydrolyzing the higher order structure are required.

Since xylanase is one of the enzymatic components in a cellulase composition produced by a microorganism, a method of producing enzymes with xylanase has a problem in production cost of the enzymes containing xylanase as a main component.

Kumar R et al., J. Ind. Microbiol. Biotechnol. 35, 377-391 (2008) discloses a method of producing xylo-oligosaccharides by hydrolyzing a biomass containing xylan and cellulose without separation and purification of xylanase from a cellulase composition. Since the cellulase composition contains various degrading enzymes, hydrolysis reaction of xylan to xylo-oligosaccharides can be carried out simultaneously with degradation of higher order structures contained in the biomass containing xylan and cellulose or hydrolysis of hemicellulose to xylan.

As described above, the method of producing xylo-oligosaccharides enzymatically with xylanase have problems of process complexity and xylanase cost. Also, the method described in Kuma R et al., J. Ind. Microbiol. Biotechnol. 35, 377-391 (2008), despite the process simplicity and the possible reduction in cost for enzyme purification, has a problem in that the produced xylo-oligosaccharides are degraded into xylose by hydrolase contained in the cellulase composition, resulting in low yield of xylo-oligosaccharides.

SUMMARY

We found that hydrolysis of a pretreated product of a biomass containing xylan and cellulose with a cellulase composition having at least activities of xylanase, cellobiohydrolase and β-glucosidase, and substantially free of β-xylosidase activity during hydrolysis against the biomass containing xylan and cellulose allows simultaneous hydrolysis reactions from hemicellulose to xylan and from xylan to xylo-oligosaccharides, as well as inhibition of hydrolysis reaction from xylo-oligosaccharides to xylose, which enable efficient production of xylo-oligosaccharides.

We thus provide:

(1) A method of producing xylo-oligosaccharides, the method comprising hydrolyzing a biomass containing xylan and cellulose with a cellulase composition,
wherein the cellulase composition has at least activities of xylanase, cellobiohydrolase and β-glucosidase and is substantially free of β-xylosidase activity against the biomass during hydrolysis.

(2) The method of producing xylo-oligosaccharides according to (1), wherein the cellulase composition comprises enzymatic active components obtained by substantial inactivation of activities of β-glucosidase and β-xylosidase against the biomass by incubation of a cellulase mixture originated from a fungus belonging to the genus *Trichoderma* having at least activities of xylanase, cellobiohydrolase, β-glucosidase and β-xylosidase against the biomass.

(3) The method of producing xylo-oligosaccharides according to (2), wherein the incubation is a process to incubate the cellulase mixture originated from a fungus belonging to the genus *Trichoderma*, whose pH is adjusted 5.5 to 8.0, at 35 to 60° C.

(4) The method of producing xylo-oligosaccharides according to any one of (1) to (3), wherein component having β-glucosidase activity in the cellulase composition comprises a component having β-glucosidase activity originated from a fungus belonging to the genus *Aspergillus*.

(5) The method of producing xylo-oligosaccharides according to any one of (1) to (4), wherein the β-xylosidase activity in the cellulase composition in terms of an enzyme activity for degrading 4-nitrophenyl-β-D-xylopyranoside is 50 to 500 U/g of proteins in the cellulase composition.

(6) The method of producing xylo-oligosaccharides according to any one of (1) to (5), wherein the β-glucosidase activity in the cellulase composition in terms of an activity for degrading 4-nitrophenyl-β-D-glucopyranoside is at least 14,000 U/g of proteins in the cellulase composition.

(7) The method of producing xylo-oligosaccharides according to any one of (1) to (6), wherein the pH condition during the hydrolysis is 6.0 to 8.0.

(8) The method of producing xylo-oligosaccharides according to any one of (1) to (7), comprising hydrolyzing a product obtained by a pretreatment of the biomass containing xylan and cellulose with an alkali.

(9) The method of producing xylo-oligosaccharides according to any one of (1) to (8), further comprising the steps of: separating the hydrolysate produced by the hydrolysis reaction into solid and liquid products; filtering the obtained liquid product through an ultrafilter; recovering the cellulase composition from the non-permeated side and obtaining xylo-oligosaccharides from the permeated side.

(10) A cellulase composition having the following enzymatic activities (a) to (d):
(a) xylanase activity in terms of an enzyme activity for degrading xylan of at least 14,000 U/g of proteins in the cellulase composition;
(b) cellobiohydrolase activity in terms of an enzyme activity for degrading 4-nitrophenyl-β-D-lactopyranoside of at least 50 U/g of proteins in the cellulase composition;
(c) β-glucosidase activity in terms of an enzyme activity for degrading 4-nitrophenyl-β-D-glucopyranoside of at least 14,000 U/g of proteins in the cellulase composition; and
(d) β-xylosidase activity in terms of an enzyme activity for degrading 4-nitrophenyl-β-D-xylopyranoside of 50 to 500 U/g of proteins in the cellulase composition.

(11) The cellulase composition according to (10), wherein the component having the β-glucosidase activity in (c) above comprises a component having β-glucosidase activity originated from a fungus belonging to the genus *Aspergillus*.

We enable convenient and efficient production of xylo-oligosaccharides from a pretreated product of a biomass containing xylan and cellulose.

DETAILED DESCRIPTION

The biomass containing xylan and cellulose is a plant-derived biomass containing at least xylan and cellulose which are raw materials of xylo-oligosaccharides.

Xylan is a member of hemicelluloses found in plant cell walls, and is a heterosaccharide in which various sugars are bound to the main chain composed of xylose units bounds by β-glycosidic linkages. Celluloses and hemicelluloses constitute plant cell walls through formation of higher order structures via hydrogen bonds or chemical bonds. Celluloses, which are main component of cell walls, have a structure in which glucose units are joined linearly by β-glycosidic linkages.

The biomass containing xylan and cellulose is not restricted as long as it is a resource containing xylan and cellulose, and plants such as seed plants, pteridophytes, bryophytes, algae and water plants, and waste building materials may be employed. Seed plants are divided into gymnosperms and angiosperms, both of which can be used preferably. Angiosperms are further divided into monocotyledons and dicotyledons. Specific examples of monocotyledons include bagasse, switchgrass, napier grass, *Erianthus*, corn stover, corncob, rice straw and wheat straw. Specific examples of dicotyledons used preferably include beet pulp, eucalyptus, oak and white birch. Preferred biomasses are bagasse, corncob, corn stover, rice straw and straw, and most preferred is bagasse, from the viewpoint of excellent property of degrading xylan and cellulose. These biomasses may be used individually or two or more of them may be used in combination.

The xylan content in the biomass containing xylan and cellulose is preferably at least 5% by weight, more preferably at least 10% by weight, still more preferably at least 20% by weight, based on the solid weight of the biomass containing xylan and cellulose. Usually, the xylan content in the biomass containing xylan and cellulose is 50% by weight or less.

The pretreatment method is not restricted and specifically, known methods such as acid treatment, sulfuric acid treatment, dilute sulfuric acid treatment, alkali treatment, hydrothermal treatment, subcritical treatment, fine grinding treatment and steaming treatment can be used. The pretreatment method is preferably an alkali treatment or a hydrothermal treatment with little degradation of xylan in the pretreatment, and most preferably an alkali treatment.

The alkali treatment may employ sodium hydroxide, potassium hydroxide, calcium hydroxide or ammonia. Sodium hydroxide is preferred from the viewpoint that it is inexpensive and easy to handle. Regarding the conditions for the alkali treatment, the solids concentration of the biomass containing xylan and cellulose in a state mixed with an alkali solution is 0.1 to 50% by weight, preferably 1 to 20% by weight, more preferably 5 to 10% by weight. When the solids concentration of the biomass containing xylan and cellulose is less than 1% by weight, the amount of water used is extremely large, leading to economic disadvantage. On the other hand, when the solids concentration of the biomass containing xylan and cellulose exceeds 20% by weight, the alkaline solution does not soak through the biomass containing xylan and cellulose, resulting in insufficient effect of the pretreatment. As for the amount of the alkali added, for example, when an aqueous sodium hydroxide solution is used, the amount of sodium hydroxide added is 0.1 to 100% by weight, preferably 1 to 50% by weight, more preferably 5 to 10% by weight, based on the solids content of the biomass containing xylan and cellulose.

The solids concentration of the biomass containing xylan and cellulose can be adjusted based on the solids weight. The solids weight can be calculated according to the following method.

The solids weight of the biomass containing xylan and cellulose can be calculated according to the following method. A grams of the biomass containing xylan and cellulose is weighed, and heated at 105° C. until a constant weight of B grams is achieved. B/A represents the solids fraction of the biomass containing xylan and cellulose, and the solids weight is defined as the value calculated by multiplying the weight of wet biomass containing xylan and cellulose by B/A. The solids weight of the pretreated product of the biomass containing xylan and cellulose can also be determined in the same manner.

When the amount of alkali added is less than 1% by weight, hydrolysis by the cellulase composition hardly progresses and sufficient yield of xylo-oligosaccharides is not obtained. On the other hand, when the addition amount exceeds 50% by weight, in addition to the fact that the amount of the alkali is large, it results in an increase in the amount of acid used for the pH adjustment during the hydrolysis reaction with the cellulase composition, which is economically disadvantageous. The temperature during the alkali treatment is preferably 10 to 200° C., more preferably 25 to 120° C., particularly preferably 75 to 100° C., from the viewpoint of sugar yield in hydrolysis. The length of time period for the alkali treatment can be appropriately set according to, for example, the amount of alkali, and is usually about 0.5 to 24 hours.

The pretreated biomass containing xylan and cellulose may be used directly for hydrolysis reaction with the cellulase composition or may be subjected to solid-liquid separation before the hydrolysis reaction. The solid product obtained by the solid-liquid separation can be used as a pretreated product of the biomass containing xylan and cellulose. As the solid-liquid separation techniques, known techniques including centrifugation such as screw decanter, filtration such as pressure or suction filtration, and membrane filtration such as microfiltration can be used. Further, the solid product in the pretreated product of the biomass containing xylan and cellulose may be washed with pure water before and after the solid-liquid separation. This washing is preferred because it can further reduce enzymatic reaction inhibitors such as lignin degradation products, and also can reduce the amount of acid required for pH adjustment during the hydrolysis reaction.

"Xylo-oligosaccharides" refer to oligosaccharides having a structure in which 2 to 6 xylose units are covalently linked, in which the xylose units are linked via β-glycosidic linkage. Xylo-oligosaccharides are referred to as xylobiose (disaccharide), xylotriose (trisaccharide), xylotetraose (tetrasaccharide), xylopentaose (pentasaccharide), or xylohexaose (hexasaccharide), depending on the number of xylose units.

The cellulase composition is a mixture of various hydrolases that hydrolyze glycosidic linkages within β-1,4-glucans. Examples of hydrolases contained in the cellulase composition include cellobiohydrolase, xylanase, endoglucanase, β-glucosidase, β-xylosidase, arabinofuranosidase, xylanesterase, ferulic acid esterase, α-glucuronidase, chitosanase, chitinase, mannanase, mannosidase, α-galactosidase, and β-galactosidase.

The cellulase composition (hereinafter referred to as "the cellulase composition") may be any those having at least activities of xylanase, cellobiohydrolase and β-glucosidase, and substantially free of β-xylosidase activity during hydrolysis against the biomass containing xylan and cellulose, and the origins of the activities are not restricted. The cellulase composition may be prepared by mixing purified enzymes, commercially available cellulase products, or commercially available products. A culture obtained by culturing microorganisms may also be used as it is as the cellulase composition. Alternatively, a mixture of enzymes purified from the culture and other commercially available enzyme products may be used.

When a cellulase composition originated from a microorganism is used as the cellulase composition, a fungus may be preferably used as the microorganism. Examples of the fungus include microorganisms belonging to the genera *Trichoderma, Aspergillus, Cellulomonas, Chlostridium, Streptomyces, Humicola, Acremonium, Irpex, Mucor* or *Talaromyces*. Among these fungi, those belonging to the genera *Trichoderma* and *Aspergillus* are preferred.

Specific examples of the fungi belonging to the genus *Trichoderma* include *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, and *Trichoderma viride* QM9123. Among these fungi belonging to the genus *Trichoderma, Trichoderma reesei* is preferred. In addition, mutant strains with improved productivity of the cellulase composition or with reduced β-xylosidase activity prepared by mutating the above-described fungi producing the cellulase composition with a mutagen, ultraviolet irradiation or the like can be preferably used.

Specific examples of the fungi belonging to the genus *Aspergillus* include *Aspergillus niger, Aspergillus fumigatus, Aspergillus aculeatus*, and *Aspergillus terreus*.

The cellulase composition may be a cellulase composition originated from one of the fungi described above or a mixture of cellulase compositions originated from two or more fungi. When using a cellulase composition originated from two or more fungi, the combination is not restricted and, for example, a mixture of a cellulase composition originated from the fungus belonging to the genus *Trichoderma* and a cellulase composition originated from the fungus belonging to the genus *Aspergillus* may be used. Specific examples of the β-glucosidase originated from a fungus belonging to the genus *Aspergillus* include Novozyme 188 (Novozymes), β-Glucosidase from *Aspergillus niger* (Megazyme), and Sumizyme BGA (Shinnihon Chemicals). Preferably, the component having the β-glucosidase activity contains a component having β-glucosidase activity originated from the fungus belonging to the genus *Aspergillus* described above.

Other than enzymes, the cellulase composition may contain contaminants such as salts and sugars, and agents for enhancing enzyme preservability, adjusting pH, or enhancing activity. A cell homogenate or a culture of a fungus that produces the cellulase composition, as well as crude enzymes obtained by removing salts, sugars and the like from the cell homogenate or the culture may also be used.

Hydrolyzation of the biomass containing xylan and cellulose using the cellulase composition can provide a hydrolysate containing xylo-oligosaccharides and glucose as main components. "Containing as main component" as used herein means that when the hydrolysate contains xylo-oligosaccharides, glucose, and xylose, the % concentration (w/v) of xylo-oligosaccharides is higher than the % concentration (w/v) of xylose. On the other hand, hydrolyzation of the biomass containing xylan and cellulose using a cellulase composition having activities of xylanase, cellobiohydrolase, β-glucosidase and β-xylosidase provides a hydrolysate containing xylose and glucose as main components.

The β-xylosidase activity is measured as an enzyme activity for degrading 4-nitrophenyl-β-D-xylopyranoside. The amount of enzyme that produces 1 µmol of 4-nitrophenol per minute is defined as 1 U. The enzyme activity is determined according to the procedures described in Reference Example 5 below.

Preferably, the cellulase composition shows substantially no β-xylosidase activity during hydrolysis of the biomass containing xylan and cellulose. The β-xylosidase activity per 1 g of proteins in the cellulase composition is preferably 500 U/g or less, more preferably 400 U/g or less, most preferably 300 U/g or less. The content of proteins in the cellulase composition is measured using Bradford method. The method of determining the content of the proteins by the Bradford method can be carried out as follows: mixing a dilute solution of the cellulase composition and a Brilliant Blue G solution; incubating the mixture for a certain period of time; and measuring the absorbance at 595 nm. The protein content in the dilute solution of the cellulase composition is calculated based on a calibration curve prepared separately using standard solutions of bovine serum albumin, from which the protein content in the cellulase composition can be determined.

The enzyme activity of xylanase is measured as a xylan-degrading activity for xylan used as a reagent. The amount of enzyme that produces 1 µmol of reducing sugar per minute is defined as 1 U. The enzyme activity is measured according to the procedures described in Reference Example 5 below.

Specifically, the xylan-degrading activity per 1 g of proteins in the cellulase composition is preferably 14,000 U/g or more, more preferably 16,000 U/g or more, still more preferably 18,000 U/g or more. The xylan-degrading activity in the cellulase composition per 1 g of proteins in the cellulase composition is usually 50,000 U/g or less.

The cellobiohydrolase activity is measured as an enzyme activity for degrading 4-nitrophenyl-β-D-lactopyranoside. The amount of enzyme that produces 1 µmol of 4-nitrophenol per minute is defined as 1 U. The enzyme activity is measured according to the procedures described in Reference Example 5 below.

Specifically, the cellobiohydrolase activity per 1 g of proteins in the cellulase composition is preferably 50 U/g or more, more preferably 65 U/g or more, still more preferably 80 U/g or more. The cellobiohydrolase activity in the cellulase composition per 1 g of proteins in the cellulase composition is usually 300 U/g or less.

The β-glucosidase activity is measured as an enzyme activity for degrading 4-nitrophenyl-β-D-glucopyranoside. The amount of enzyme that produces 1 µmol of 4-nitrophenol per minute is defined as 1 U. The enzyme activity is measured according to the procedures described in Reference Example 5 below.

Specifically, the β-glucosidase activity per 1 g of proteins in the cellulase composition may be any value not less than 1000 U/g, and is preferably 10,000 U/g or more, more preferably 14,000 U/g or more, still more preferably 16,000 U/g or more, most preferably 18,000 U/g or more. The β-glucosidase activity in the cellulase composition per 1 g of proteins in the cellulase composition is usually 50,000 U/g or less.

The enzymatic components in the cellulase composition can be identified, in addition to the above-mentioned method of measuring the enzyme activities, by: separating the enzymatic components using a known technique such as gel filtration, ion exchange, or two-dimensional electrophoresis; analyzing the amino acid sequence of the separated component (N-terminal analysis, C-terminal analysis, and mass spectrometry); and comparing the results with database.

The pretreated product of the biomass containing xylan and cellulose can be hydrolyzed with a cellulase composition having at least activities of xylanase, cellobiohydrolase and β-glucosidase and substantially free of β-xylosidase activity during hydrolysis against the biomass containing xylan and cellulose to obtain a hydrolysate containing xylo-oligosaccharides.

The conditions of hydrolysis are not restricted as long as the cellulase composition can hydrolyze the pretreated product of the biomass to give xylo-oligosaccharides. The reaction temperature during the hydrolysis is kept preferably at 50° C. or lower, more preferably at 30 to 45° C. When the reaction temperature is kept at 30° C. to 45° C., activities of various hydrolases contained in the cellulase composition do not decrease, which enables recycling of the cellulase composition after the hydrolysis reaction.

The preferred pH in the hydrolysis reaction is not restricted, and the pH is preferably 4.5 to 8.0, more preferably 6.0 to 8.0, still more preferably 6.5 to 7.5. The pH range from 6.5 to 7.5 has the effect of increasing the yield of xylo-oligosaccharides, and can maintain the activities of xylanase, cellobiohydrolase and β-glucosidase in the cellulase composition at high levels even after the hydrolysis.

Adjustment of pH during the hydrolysis may be carried out by individually adjusting the pH values of the pretreated product of the biomass containing xylan and cellulose and of the cellulase composition before the addition of the cellulase composition to the pretreated product of the biomass containing xylan and cellulose. Alternatively, the pH value may be adjusted after the addition of the cellulase composition to the pretreated product of the biomass containing xylan and cellulose. Preferably, pH values are individually adjusted before the addition of the cellulase composition to the pretreated product of the biomass containing xylan and cellulose.

For the adjustment of the pH value, an acid, alkali, or pH buffer solution can be used. The types of the acid, alkali or pH buffer solution is not restricted as long as it is capable of adjusting the pH to a predetermined value. Examples of the acid include hydrochloric acid, sulfuric acid, nitric acid, phosphoric acid, formic acid and acetic acid. Among them, hydrochloric acid and sulfuric acid are preferred from the viewpoint that they are inexpensive and have the ability to adjust the pH to a desired value with a small amount. Examples of the alkali include sodium hydroxide, potassium hydroxide, calcium hydroxide, ammonia, sodium carbonate, calcium carbonate, and trisodium phosphate. Among them, sodium hydroxide and potassium hydroxide are preferred from the viewpoint that they are inexpensive and have the ability to adjust the pH to a desired value with a small amount. When a pH buffer solution is used, examples of the pH buffer solution used include acetate buffer, citrate buffer, phosphate buffer and Tris-HCl buffer. Among them, phosphate buffer and Tris-HCl buffer are preferred from the viewpoint that the pH to be adjusted is pH 6.0 to 8.0.

During the hydrolysis reaction, the reaction is preferably carried out under stirring to promote the contact between the pretreated product of the biomass containing xylan and cellulose and the cellulase composition and to make the sugar concentration of the hydrolysate uniform. The concentration of the solids in the pretreated product of the biomass containing xylan and cellulose during the hydrolysis is preferably 1 to 30% by weight, more preferably 3 to 20% by weight, still more preferably 5 to 10% by weight.

The reaction time of the hydrolysis is preferably 1 to 144 hours, more preferably 3 to 72 hours, still more preferably 6 to 24 hours, most preferably 6 to 10 hours.

In the hydrolysis reaction with hydrolases contained in the cellulase composition, cellulose contained in the pretreated product of the biomass containing xylan and cellulose is degraded by cellobiohydrolase into cello-oligosaccharides, which in turn are hydrolyzed by β-glucosidase into glucose. On the other hand, xylan contained in the pretreated product of the biomass containing xylan and cellulose is hydrolyzed by xylanase into xylo-oligosaccharides.

Xylan is a member of hemicelluloses that are found in plant cell walls. Hemicelluloses constitute plant cell walls through formation of higher order structures via hydrogen bonds or chemical bonds with cellulose. We found that use of a cellulase composition having not only xylanase activity but also cellobiohydrolase and β-glucosidase activities in hydrolysis reaction enables efficient production of xylo-oligosaccharides.

In the hydrolysate, in addition to xylo-oligosaccharides, for example, monosaccharides such as glucose, xylose, mannose, arabinose, and galactose, and oligosaccharides such as cellobiose, cellotetraose, mannobiose, and galactobiose produced by hydrolases contained in the cellulase composition may be contained.

When a cellulase composition has activities of xylanase, cellobiohydrolase, β-glucosidase and β-xylosidase, the cellulase composition can be prepared through the following processes.

The cellulase composition is suspended or dissolved in an aqueous medium. The pH of the obtained suspension or aqueous solution of the cellulase composition is adjusted to 5.5 to 8.0 and incubated at 35° C. to 60° C. When the cellulase composition is suspended, a condition wherein no substrate is added is preferred. The pH is adjusted more preferably to 6.0 to 8.0, still more preferably 6.5 to 8.0. The incubation time is not particularly restricted and is preferably within 24 hours, more preferably within 12 hours, still more preferably 0.1 to 8 hours, most preferably 2 to 6 hours. When the cellulase composition is suspended, the concentration of the cellulase composition is not particularly restricted and is preferably adjusted to 0.1 to 100 g/L, more preferably 1 to 50 g/L, still more preferably 2 to 10 g/L in terms of protein concentration. The protein concentration is measured by Bradford method. To adjust the pH of the suspension or aqueous solution of the cellulase composition, the above-mentioned acids, alkalis, or pH buffer solutions used in the pH adjustment of the pretreated product of the biomass containing xylan and cellulose can be used.

As described in detail in the Examples below, the above-described treatment remarkably reduces β-xylosidase activity, while reductions in activities of xylanase, cellobiohydrolase and β-glucosidase are relatively small. Thus, the β-xylosidase activity in the cellulase composition can be considerably selectively reduced. Thus, for example, even when the β-xylosidase activity in the cellulase composition before the incubation is over 500 U/g of proteins in the cellulase composition, the incubation can reduce the β-xylosidase activity to 500 U/g or lower, preferably 400 U/g or lower, still more preferably 300 U/g or lower, per gram of proteins in the cellulase composition, while maintaining the activities of xylanase, cellobiohydrolase and β-glucosidase within each of the preferred ranges described above. Cellulase compositions originated from fungi often have a β-xylosidase activity exceeding 500 U/g of proteins in the cellulase composition. Even such cellulase compositions can be made into those which are capable of being used in the method and substantially free of β-xylosidase activity, via the above simple incubation. "Cellulase compositions originated from fungi" includes those to which one or two or more of xylanase, cellobiohydrolase and β-glucosidase is/are separately and additively added as long as cellulase compositions produced by fungi are contained. Since the β-xylosidase activity per gram of proteins in cellulase compositions is usually 50 U/g or more, the β-xylosidase activity is preferably 50 to 500 U/g.

Methods of recovering a cellulase composition from a hydrolysate obtained in a hydrolysis reaction include, but not limited to, a method comprising filtering a hydrolysate through an ultrafilter and then recovering a cellulase composition from the non-permeated side; and a method comprising separating a hydrolysate into solid and liquid products and then eluting the cellulase composition from the solid product.

Among these, the method of recovering a cellulase composition using an ultrafilter is preferred. The recovering method using an ultrafilter is preferred because it can give a sugar solution containing a cellulase composition on the non-permeated side and a sugar solution containing xylo-oligosaccharides on the permeated side. The purity of the cellulase composition can be further increased by adding water to the nonpermeate and repeating the filtration through the ultrafilter again.

When recovering the cellulase composition using an ultrafilter, the molecular cutoff is preferably 1,000 to 50,000, more preferably 5,000 to 50,000, still more preferably 10,000 to 30,000.

Examples of ultrafilter material which can be used include polyether sulfone (PES), polysulfone (PS), polyacrylonitrile (PAN), polyvinylidene difluoride (PVDF), regenerated cellulose, cellulose, cellulose ester, sulfonated polysulfone, sulfonated polyether sulfone, polyolefin, polyvinyl alcohol, polymethyl methacrylate, and polytetrafluoroethylene. Since regenerated cellulose, cellulose, and cellulose ester are degraded by the cellulase composition, ultrafilters made of synthetic polymers such as PES and PVDF are preferably used.

Filtration using ultrafilters includes dead end filtration and cross flow filtration, and cross flow filtration is preferred from the viewpoint of suppression of membrane fouling. Forms of the ultrafilter which can be used include suitable forms such as flat, spiral, tubular, and hollow fiber types. Specifically, G-5 type, G-10 type, G-20 type, G-50 type, PW type and HWSUF type from DESAL; HFM-180, HFM-183, HFM-251, HFM-300, HFK-131, HFK-328, MPT-U20, MPS-U20P, MPS-U20S; Synder SPE1, SPE3, SPE5, SPE10, SPE30, SPV5, SPV50, SOW30 from KOCH; Microza (registered trademark) UF series manufactured by Asahi Kasei, whose molecular cutoff is 3,000 to 10,000; and NTR7410 and NTR7450 manufactured by Nitto Denko, may be used.

In addition, a sugar solution containing xylo-oligosaccharides obtained may be concentrated to further increase the sugar concentration. Examples of the concentration process include concentration by evaporation, concentration under reduced pressure, and concentration through a membrane. Among these, a filtering method through a nanofiltration membrane and/or reverse osmosis membrane, disclosed in WO2010/067785, may preferably be used to obtain a sugar concentration in which sugar components are concentrated, which method uses less energy and is capable of removing fermentation inhibitors contained in a sugar solution.

Xylo-oligosaccharides obtained may be used directly as a raw material for, for example, foods and feeds. Alternatively, xylo-oligosaccharides with enhanced purity achieved by known methods may be used as a raw material for, for example, foods and feeds.

Furthermore, various chemicals can be produced by using the sugar solutions containing glucose and xylose separated by the above method as fermentation raw materials and growing microorganisms capable of producing the chemicals. "Using the sugar solutions as fermentation raw materials and growing microorganisms" means using the sugar components or amino sources contained in the sugar solution as nutrients for the microorganisms and growing or maintaining the growth of the microorganisms. Specific examples of the chemicals include substances mass-produced in the fermentation industry such as alcohols, organic acids, amino acids and nucleic acids. Such chemicals are produced and accumulated inside and outside the microorganisms through metabolic processes of the sugar components in a sugar solution used as carbon sources. Specific examples of the chemical products capable of being produced by microorganisms include alcohols such as ethanol, 1,3-propanediol, 1,4-butanediol and glycerol; organic acids such as acetic acid, lactic acid, pyruvic acid, succinic acid, malic acid, itaconic acid and citric acid; nucleosides such as inosine and guanosine; nucleotides such as inosinic acid and guanylic acid; and amine compounds such as cadaverine. Further, the sugar solution obtained can be applied for the production of, for example, enzymes, antibiotics, and recombinant proteins. Any microorganisms capable of efficiently producing chemicals of interest can be used in the production of such chemicals, including microorganisms such as *Escherichia coli*, yeasts and fungi (filamentous fungi and basidiomycetes).

EXAMPLES

Our methods will now be described in detail with reference to Examples and Comparative Examples.

Reference Example 1 Pretreatment of Biomass Containing Xylan and Cellulose

Bagasse as a biomass containing xylan and cellulose was pretreated. Five grams of bagasse was weighed and heated to 105° C. The solid content fraction of the bagasse was calculated based on the change in weight through the heating. The wet bagasse was multiplied by the water content rate to obtain the solid content weight. Bagasse in an amount of 100 g was immersed in an aqueous sodium hydroxide solution such that the solids concentration of the mixture with the sodium hydroxide solution was 5% by weight and such that the amount of sodium hydroxide added relative to the bagasse solids content was 10% by weight, and then the mixture was subjected to pretreatment at 80° C. for 3 hours. The mixture was separated into solid and liquid products by centrifugation (3,000 G, 10 minutes). The solid product was washed with pure water and then used in the following experiment as a pretreated product of the biomass containing xylan and cellulose.

Reference Example 2 Preparation of Cellulase Composition

Preculture

A 500 mL Erlenmeyer flask with baffles was charged with 100 mL of a solution of 5% (w/vol) corn steep liquor, 2% (w/vol) glucose, 0.37% (w/vol) ammonium tartrate, 0.14% (w/vol) ammonium sulfate, 0.2% (w/vol) potassium dihydrogenphosphate, 0.03% (w/vol) calcium chloride dihydrate, 0.03% (w/vol) magnesium sulfate heptahydrate, 0.02% (w/vol) zinc chloride, 0.01% (w/vol) iron(III) chloride hexahydrate, 0.004% (w/vol) copper(II) sulfate pentahydrate, 0.0008% (w/vol) manganese chloride tetrahydrate, 0.0006% (w/vol) boric acid, and 0.0026% (w/vol) hexaammonium heptamolybdate tetrahydrate in distilled water, and then the mixture was autoclave-sterilized at 121° C. for 15 minutes. After allowing the flask to cool, each 0.01% (w/vol) of PE-M and Tween 80 independently autoclave-sterilized at 121° C. for 15 minutes separately were added to the solution to prepare a preculture medium. Into 100 mL of this preculture medium, $1\times10^5$ cells/mL of *Trichoderma reesei* ATCC66589 (purchased from ATCC) was inoculated and cultured under shaking at 180 rpm at 28° C. for 72 hours to obtain a preculture (shaker: TAITEC BIO-SHAKER BR-40LF).

Main Culture

A 5 L stirring jar (DPC-2A manufactured by ABLE) was charged with 2.5 L of a solution of 5% (w/vol) corn steep liquor, 2% (w/vol) glucose, 10% (w/vol) cellulose (Avicel), 0.37% (w/vol) ammonium tartrate, 0.14% (w/vol) ammonium sulfate, 0.2% (w/vol) potassium dihydrogenphosphate, 0.03% (w/vol) calcium chloride dihydrate, 0.03% (w/vol) magnesium sulfate heptahydrate, 0.02% (w/vol) zinc chloride, 0.01% (w/vol) iron(III) chloride hexahydrate, 0.004% (w/vol) copper(II) sulfate pentahydrate, 0.0008% (w/vol) manganese chloride tetrahydrate, 0.0006% (w/vol) boric acid, and 0.0026% (w/vol) hexaammonium heptamolybdate tetrahydrate in distilled water, and then the mixture was autoclave-sterilized at 121° C. for 15 minutes. After allowing the flask to cool, each 0.1% of PE-M and Tween 80 independently autoclave-sterilized at 121° C. for 15 minutes separately were added to the solution to prepare a main culture medium. Into 2.5 L of this main culture medium, 250 mL of *Trichoderma reesei* PC3-7 precultured in the above-described preculture medium was inoculated. Next, cells were cultured at 28° C. for 87 hours at 300 rpm at an aeration level of 1 vvm, and centrifuged. The supernatant was then filtered through a membrane filter (Stericup-GV, made of PVDF, manufactured by Millipore). To the prepared culture, β-glucosidase (Novozyme 188) was added in an amount of 1/100 in terms of a protein weight ratio to obtain a cellulase composition.

Since LA Grange D C et al. (Appl. Environ. Microbiol. 62, 1036-1044, 1996), Boer H et al. (Biotechnol. Bioeng. 69, 486-494, 2000), and William J C et al. (Eur. J. Biochem. 165, 333-341, 1987) disclose that optimum pH values of xylanase, cellobiohydrolase, and β-glucosidase in a cellulase composition originated from filamentous fungi are pH 5.0 to 6.0, pH 5.0, and pH 5.0, respectively, the optimum pH of the cellulase composition obtained in the Reference Example for enzymatic reaction was estimated to be pH 5.

Reference Example 3 Measurement of Protein Concentration

A commercially available reagent for measuring protein concentration (Quick Start Bradford protein assay, manufactured by Bio-Rad) was used for the measurement of protein concentration of cellulase compositions. Five microliters of a diluted solution of cellulase composition was added to 250 µL of the protein concentration measurement reagent which was previously returned to room temperature. After leaving the mixture to stand at room temperature for 5 minutes, the absorbance at 595 nm was measured using a microplate reader (POWERSCAN HT, manufactured by Sumitomo Dainippon Pharma). Using an aqueous bovine serum albumin solution as a standard, the protein concentration of the cellulase composition solution was calculated based on the calibration curve.

Reference Example 4 Measurement of Sugar Concentration

Quantitative analyses of xylo-oligosaccharides, glucose and xylose were carried out using LaChrom Eite high performance liquid chromatography (HITACHI) under the following conditions.

The quantitative analyses were based on calibration curves prepared with standards of xylobiose, xylotriose, xylotetraose, xylopentaose and xylohexaose which are xylo-oligosaccharides, glucose and xylose. The xylo-oligosaccharides described in this example refer to xylo-oligosaccharides in which 2 to 6 xylose units are bound by β-glycosidic bonds.

Column: KS802, KS803 (Shodex)
Mobile phase: water
Detection method: RI
Flow rate: 0.5 mL/min
Temperature: 75° C.

Reference Example 5 Method of Measuring Enzyme Activity

Four enzyme activities: 1) β-xylosidase activity; 2) xylan degrading activity; 3) cellobiohydrolase activity; and 4) β-glucosidase activity were evaluated through measurement at pH 5 which is the optimum pH for enzymatic reactions of the cellulase composition obtained in Reference Example 2 according to the following procedure.

1) β-xylosidase Activity 4-nitrophenyl-β-D-xylopyranoside (manufactured by Sigma-Aldrich) was dissolved in 50 mM sodium acetate buffer (pH 5.0) to a concentration of 1 mM to obtain a substrate solution. The enzyme solution in an amount of 10 µL was added to 90 µL of the substrate solution, and the mixture was left to stand for reaction at 30° C. After 10 minutes, the reaction was stopped by adding 10 µL of sodium carbonate solution. Then, 4-nitrophenol was quantified by measuring the absorbance at 405 nm. In the above reaction system, the amount of enzyme that produces 1 µmol of 4-nitrophenol per minute is defined as 1 U. The activity value (U/mL) was calculated according to the following formula:

β-xylosidase Activity (U/mL)=4-nitrophenol (µmol/ml)×volume of reaction solution (µl)/((reaction time (min)×volume of enzyme solution (µL))× dilution ratio (fold).

2) Xylan-Degrading Activity

Xylan (Xylan from Birch wood, manufactured by Fluka) was suspended in 50 mM sodium acetate buffer (pH 5.0) to a concentration of 1% by weight to obtain a substrate solution. The enzyme solution in an amount of 5 µL was added to 500 µL of the substrate solution dispensed, and the mixture was allowed to react while mixing with rotation at 50° C. The reaction time, which was basically 30 minutes, varied appropriately from 10 to 60 minutes depending on the enzyme activity. After the reaction, the tube was centrifuged and the concentration of reducing sugar in the supernatant was measured by DNS method. In the above reaction system, the amount of enzyme that produces 1 µmol of reducing sugar per minute is defined as 1 U. The activity value (U/mL) was calculated according to the following formula:

Xylan degrading activity (U/mL)=concentration of reducing sugar (g/L)×1000×505 (µL)/(150.13× reaction time (min)×5 (µL)).

3) Cellobiohydrolase Activity 4-nitrophenyl-β-D-lactopyranoside (manufactured by Sigma-Aldrich) was dissolved in 50 mM sodium acetate buffer (pH 5.0) to a concentration of 1 mM to obtain a substrate solution. The enzyme solution in an amount of 10 µL was added to 90 µL of the substrate solution, and the mixture was left to stand for reaction at 30° C. After 10 minutes, the reaction was stopped by adding 10 µL of sodium carbonate solution. Then, 4-nitrophenol was quantified by measuring the absorbance at 405 nm. In the above reaction system, the amount of enzyme that produces 1 µmol of 4-nitrophenol per minute is defined as 1 U. The activity value (U/mL) was calculated according to the following formula:

Cellobiohydrolase activity (U/mL)=4-nitrophenol (µmol/ml)×volume of reaction solution (µl)/ (reaction time (min)×volume of enzyme solution (µL))×dilution ratio (fold).

Since the detection sensitivity decreases when the activity value is less than 5 U/g, the detection limit of the measurement method is less than 5 U/g.

4) β-Glucosidase Activity (BGL Activity)

4-nitrophenyl-β-D-glucopyranoside (manufactured by Sigma-Aldrich) was dissolved in 50 mM sodium acetate buffer (pH 5.0) to a concentration of 1 mM to obtain a substrate solution. The enzyme solution in an amount of 10 µL was added to 90 µL of the substrate solution, and the mixture was left to stand for reaction at 30° C. After 10 minutes, the reaction was stopped by adding 10 µL of sodium carbonate solution. Then, 4-nitrophenol was quantified by measuring the absorbance at 405 nm. In the above reaction system, the amount of enzyme that produces 1 µmol of 4-nitrophenol per minute is defined as 1 U. The activity value (U/mL) was calculated according to the following formula:

β-glucosidase activity (U/mL)=4-nitrophenol (µmol/ ml)×volume of reaction solution (µl)/((reaction time (min)×volume of enzyme solution (µL))× dilution ratio (fold).

Since the detection sensitivity decreases when the activity value is less than 50 U/g, the detection limit of the measurement method is 50 U/g.

Comparative Example 1 Hydrolysis Reaction Using Xylanase

The solids content fraction of the pretreated product of the biomass containing xylan and cellulose prepared according to Reference Example 1 was determined in the same manner as in Reference Example 1 for the solids content fraction of bagasse, and 1 g of solids was weighed into 50 mL tubes. Pure water was added such that the solids concentration of the pretreated product of the biomass containing xylan and cellulose at the start of reaction was 10% by weight, while pH was adjusted to 5.0 with dilute hydrochloric acid. Cellulosin TP25 (manufactured by HBI) as xylanase for industrial use, was added to the pH-adjusted pretreated product of the biomass containing xylan and cellulose such that the xylan-degrading activity was 250 U per gram of solids of the pretreated product of the biomass containing xylan and cellulose as measured by the method described in Reference Example 5. Next, the mixture was mixed with rotation using a hybridization rotator (SN-06BN manufactured by Nissin Rika) under reaction conditions which are the recommended pH and temperature conditions for Cellulosin TP25, that is, at pH 5.0 and 40° C., for 8 hours. Sugar components contained in the supernatant of the obtained hydrolysate were analyzed by the method described in Reference Example 4.

Example 1 Hydrolysis Reaction Using the Cellulase Composition, Which Cellulase Composition was Incubated Under Specific pH and Temperature Conditions The pH value of the cellulase composition obtained in Reference Example 2 was adjusted to from 5.5 to 8.0 with 1 N aqueous sodium hydroxide solution. After diluting the cellulase composition with water such that the protein concentration was 4 g/L, the obtained dilution was incubated at 35 to 60° C. Detailed incubation conditions are shown in Table 1. Table 1 shows comparison between the results of determination of activities of cellobiohydrolase, β-glucosidase, xylan-degrading and β-xylosidase in the cellulase compositions incubated under each condition using the method described in Reference Example 5, and the results of activities before incubation. As shown in the results, under any incubation conditions, the β-xylosidase activities at the pH optimum for the enzyme activity were reduced to values which were substantially inactive for hydrolysis against biomass, while the activities of cellobiohydrolase, β-glucosidase and xylan-degrading kept 60% or more, demonstrating that (β-xylosidase was selectively deactivated under any incubation condition.

Next, hydrolysis reaction of the biomass containing xylan and cellulose was carried out using, as the cellulase composition, cellulase compositions in which the β-xylosidase activity was selectively deactivated via incubation under the respective conditions. Based on the xylan-degrading activity before incubation determined according to Reference Example 5, the cellulase composition was added to the pretreated product of the biomass containing xylan and cellulose, whose pH was adjusted to 7.0, such that the xylan-degrading activity was 250 U per gram of solids of the pretreated product of biomass containing xylan and cellulose. The mixture was mixed with rotation using a hybridization rotator at pH 7.0 at 40° C. for 8 hours. Sugar components contained in the supernatant of the obtained hydrolysate were analyzed by the method described in Reference Example 4 and the results are shown in Table 2. We found that more xylo-oligosaccharides were obtained compared to the hydrolysis reaction using xylanase in Comparative Example 1 or the non-incubated cellulase composition in Comparative Example 2.

TABLE 1

| Enzyme | Incubation conditions | pH during activity measurement pH | Temperature during activity measurement °C. | β-xylosidase activity (U/g) | Xylan-degrading activity (U/g) | Cellobiohydrolase activity (U/g) | β-glucosidase activity (U/g) |
| --- | --- | --- | --- | --- | --- | --- | --- |
| Xylanase (Reference Example 1) | — | 5.0 | 30 | 20 | $40,000 \times 10^2$ | below detection limit | below detection limit |
| Filamentous fungi-originated cellulose (Reference Example 2) | — | 5.0 | 30 | 650 | 33,200 | 128 | 26,100 |
| Filamentous fungi-originated cellulose (Example 1) | pH 5.5, 60° C., 1 h | 5.0 | 30 | 244 | 29,000 | 117 | 25,800 |
| | pH 7.5, 40° C., 2 h | 5.0 | 30 | 147 | 31,300 | 120 | 25,400 |
| | pH 7.5, 40° C., 6 h | 5.0 | 30 | 135 | 27,400 | 93 | 25,200 |
| | pH 7.6, 44° C., 4 h | 5.0 | 30 | 98 | 20,800 | 88 | 20,800 |
| | pH 8.0, 35° C., 10 min | 5.0 | 30 | 103 | 26,200 | 103 | 25,000 |

TABLE 2

| Enzyme | Incubation conditions | pH during hydrolysis | Temperature during hydrolysis (° C.) | Xylo-oligosaccharides (g/L) | Glucose (g/L) | Xylose (g/L) |
| --- | --- | --- | --- | --- | --- | --- |
| Xylanase (Reference Example 1) | — | 5.0 | 40 | 7 | 2 | 1 |
| | — | 7.0 | 40 | 5 | 2 | 1 |
| Filamentous fungi-derived cellulose (Reference Example 2) | — | 7.0 | 40 | 5 | 37 | 15 |
| Filamentous fungi-derived cellulose (Example 1) | pH 5.5, 60° C., 1 h | 7.0 | 40 | 15 | 35 | 6 |
| | pH 7.5, 40° C., 2 h | 7.0 | 40 | 16 | 36 | 5 |
| | pH 7.5, 40° C., 6 h | 7.0 | 40 | 14 | 34 | 6 |
| | pH 7.6, 44° C., 4 h | 7.0 | 40 | 13 | 32 | 5 |
| | pH 8.0, 35° C., 10 min | 7.0 | 40 | 14 | 34 | 6 |

Example 2

A hydrolysis reaction was carried out in the same manner as in the hydrolysis reaction in Example 1 except that the reaction was carried out at pH 6.0 to 8.0 at 40° C. using the cellulase composition which was incubated at pH 7.5 at 40° C. for 2 hours. Sugar components contained in the supernatant of the obtained hydrolysate were analyzed and results are shown in Table 3. From the results, we found that the hydrolysis reaction under any of the pH conditions can provide more xylo-oligosaccharides compared to the hydrolysis reaction using xylanase in Comparative Example 1.

TABLE 3

| Reaction pH | Reaction temperature (° C.) | Xylo-oligosaccharide (g/L) | Glucose (g/L) | Xylose (g/L) |
| --- | --- | --- | --- | --- |
| 6.0 | 40 | 8 | 41 | 15 |
| 6.5 | 40 | 16 | 36 | 9 |
| 7.0 | 40 | 16 | 36 | 5 |
| 7.5 | 40 | 14 | 31 | 6 |
| 8.0 | 40 | 9 | 27 | 5 |

Example 3

The cellulase composition in Reference Example 2 was pre-incubated at pH 7.5 at 40° C. for 2 hours before the addition of β-glucosidase (Novozyme 188). The β-glucosidase activity after the incubation was 124 U/g. Then, β-glucosidase (Novozyme 188) was added to the incubated cellulase composition such that each β-glucosidase activity was 1,000 U/g, 5,000 U/g, 10,000 U/g, 14,000 U/g, 18,000 U/g, and 25,000 U/g, respectively, to obtain cellulase compositions used in the present Example. A hydrolysis reaction was carried out in the same manner as in the hydrolysis reaction in Example 2 except for using these cellulase compositions at pH 7.0 at 40° C. Sugar components contained in the supernatant of the obtained hydrolysate were analyzed by the method described in Reference Example 4 and the results are shown in Table 4. From the results, we found that the cellulase composition containing larger amount of β-glucosidase added provides improved xylo-oligosaccharides yield.

TABLE 4

| β-glucosidase activity (U/g) | Xylo-oligosaccharide (g/L) | Glucose (g/L) | Xylose (g/L) |
| --- | --- | --- | --- |
| 1,000 | 9 | 17 | 6 |
| 5,000 | 9 | 22 | 5 |
| 10,000 | 10 | 27 | 5 |
| 14,000 | 13 | 30 | 5 |
| 18,000 | 14 | 33 | 6 |
| 25,000 | 16 | 36 | 5 |

Example 3

A hydrolysis reaction was carried out in the same manner as in the hydrolysis reaction in Example 1 except that the reaction was carried out at pH 7.0 at 35 to 45° C. using the cellulase composition which was incubated at pH 7.5 at 40° C. for 2 hours. After mixing the reaction with rotation for 8 hours, the obtained hydrolysate was centrifuged at 8,000 g for 5 minutes and separated into liquid and solid products. The liquid product was filtered through a microfiltration membrane (Millex-GV, manufactured by Millipore) having a pore size of 0.22 μm to obtain a filtrate. Further, the obtained filtrate was filtered through an ultrafilter (Vivaspin 20-10K, manufactured by Sartopore) having a molecular cutoff of 10,000 to obtain a permeate and a nonpermeate.

The results obtained by measuring the sugar contents contained in the permeate are shown in Table 4. The results obtained by determining the activities of enzymes contained in the nonpermeate in the same manner as in Reference Example 5 are shown in Table 5. Table 6 shows relative activities of enzymes in the nonpermeate when each enzyme activity before incubating the cellulase composition is taken as 100. From these results, we found that a cellulase composition which maintains high activities of xylanase, cellobiohydrolase and β-glucosidase even after hydrolysis can be recovered from a hydrolysate in which xylo-oligosaccharides have been produced.

TABLE 5

| Reaction pH | Reaction temperature (° C.) | Xylo-oligosaccharide (g/L) | Glucose (g/L) | Xylose (g/L) |
| --- | --- | --- | --- | --- |
| 7.0 | 35 | 12 | 34 | 9 |
| 7.0 | 40 | 16 | 36 | 5 |
| 7.0 | 45 | 17 | 34 | 5 |

TABLE 6

| Reaction pH | Reaction temperature (° C.) | β-xylosidase activity (%) | Xylan-degrading activity (%) | Cellobiohydrolase activity (%) | β-glucosidase activity (%) |
| --- | --- | --- | --- | --- | --- |
| 7.0 | 35 | 15 | 66 | 58 | 78 |
| 7.0 | 40 | 10 | 58 | 41 | 76 |
| 7.0 | 45 | 7 | 40 | 32 | 67 |

INDUSTRIAL APPLICABILITY

Xylo-oligosaccharides obtained can be used as a raw material for, for example, foods and feeds containing xylo-oligosaccharides.

The invention claimed is:

1. A method of producing a cellulase composition, comprising incubating a cellulase mixture not containing a biomass containing xylan and cellulose, having activities of xylanase, cellobiohydrolase, β-glucosidase and β-xylosidase originated from the genus *Trichoderma* and β-glucosidase activity originated from the genus *Aspergillus* at a temperature of 35° C. to 60° C. and pH of 5.5 to 8.0 to selectively reduce the activity of β-xylosidase while maintaining the activity of β-glucosidase, xylanase and cellobiohydrolase, to attain
    a β-glucosidase activity in said cellulase composition in terms of an enzyme activity for degrading 4-nitrophenyl-β-D-glucopyranoside of at least 14,000 U/g of proteins in said cellulase composition;
    a β-xylosidase activity m said cellulase composition in terms of an enzyme activity for degrading 4-nitrophenyl-β-D-xylopyranoside of 50 to 300 U/g of proteins in said cellulase composition;
    a xylanase activity in said cellulase composition in terms of an enzyme activity for degrading xylan of at least 18,000 U/g of proteins in said cellulase composition; and
    a cellobiohydrolase activity in said cellulase composition in terms of an enzyme activity for degrading 4-nitrophenyl-β-D-lactopyranoside of at least 80 U/g of proteins in said cellulase composition.

2. A method of producing xylo-oligosaccharides comprising hydrolyzing a biomass containing xylan and cellulose with the cellulase composition produced by the method according to claim 1.

3. The method according to claim 2, wherein the pH condition during the hydrolysis is 6.0 to 8.0.

4. The method according to claim 2, comprising hydrolyzing a product obtained by a pretreatment of said biomass containing xylan and cellulose with an alkali.

5. The method according to claim 2, further comprising the steps of: separating the hydrolysate produced by the hydrolysis reaction into solid and liquid products; filtering the obtained liquid product through an ultrafilter; recovering the cellulase composition from the non-permeated side and obtaining xylo-oligosaccharides from the permeated side.

6. A method of producing cellulase composition comprising:
    a) incubating a cellulase mixture not containing a biomass containing xylan and cellulose, having the activities of xylanase, cellobiohydrolase, β-glucosidase and β-xylosidase activities originated from genus *Trichoderma* at a temperature of 35° C. to 60° C. and pH of 5.5 to 8.0 to selectively reduce the activity of both β-glucosidase and β-xylosidase while maintaining the activity of xylanase and cellobiohydrolase; and
    b) adding β-glucosidase into the cellulase mixture of a), to attain a β-glucosidase activity in said cellulase composition in terms of an enzyme activity for degrading 4-nitrophenyl-β-D-glucopyranoside of at least 14,000 U/g of proteins in said cellulase composition;
    a β-xylosidase activity in said cellulase composition in terms of an enzyme activity for degrading 4-nitrophenyl-β-D-xylopyranoside of 50 to 300 U/g of proteins in said cellulase composition;
    a xylanase activity in said cellulase composition in terms of an enzyme activity for degrading xylan of at least 18,000 U/g of proteins in said cellulase composition; and
    a cellobiohydrolase activity in said cellulase composition in terms of an enzyme activity for degrading 4-nitrophenyl-β-D-lactopyranoside of at least 80 U/g of proteins in said cellulase composition.

7. A method of producing xylo-oligosaccharides comprising hydrolyzing a biomass containing xylan and cellulose with the cellulase composition produced by the method according to claim 6.

8. The method according to claim 7, wherein the pH condition during the hydrolysis is 6.0 to 8.0.

9. The method according to claim 7, wherein the biomass is obtained by a pretreatment with an alkali.

10. The method according to claim 7, further comprising the steps of: separating the hydrolysate produced by the hydrolysis reaction into solid and liquid products; filtering the obtained liquid product through an ultrafilter; recovering the cellulase composition from the non-permeated side and obtaining xylo-oligosaccharides from the permeated side.

* * * * *